(12) United States Patent
Sheppard et al.

(10) Patent No.: US 6,627,729 B1
(45) Date of Patent: Sep. 30, 2003

(54) TML PEPTIDES

(75) Inventors: Paul O. Sheppard, Redmond, WA (US); Theresa A. Deisher, Seattle, WA (US); Stephen R. Jaspers, Edmonds, WA (US); Paul D. Bishop, Fall City, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/404,417

(22) Filed: Sep. 23, 1999

Related U.S. Application Data

(63) Continuation-in-part of application No. 09/046,479, filed on Mar. 23, 1998, now Pat. No. 6,291,653.
(60) Provisional application No. 60/041,102, filed on Mar. 24, 1997.

(51) Int. Cl.$^7$ .............................. C07K 7/06; C07K 7/08
(52) U.S. Cl. ...................... 530/326; 530/327; 530/328; 530/309
(58) Field of Search ............................... 530/328, 327, 530/326, 309

(56) References Cited

U.S. PATENT DOCUMENTS

| | | | |
|---|---|---|---|
| 5,006,469 A | 4/1991 | Adelman et al. | 435/240.1 |
| 5,470,830 A | 11/1995 | Macielag et al. | 514/13 |
| 6,380,158 B1 * | 4/2002 | Sheppard | 514/12 |

FOREIGN PATENT DOCUMENTS

| WO | 98/42840 | 10/1998 |
|---|---|---|

OTHER PUBLICATIONS

U.S. Application No. 09/608,810, filed Jun. 30, 2000.
Pearson et al., *Gastrointestinal Hormones in Medicine* 22: 753–774, 1993.
Daikh et al., *DNA* 8: 615–621, 1989.
INC2207941, LIFESEQ™ Clone Information Results, Incyte Pharmaceuticals Inc., 1996.
INC1328219, LIFESEQ™ Clone Information Results, Incyte Pharmaceuticals Inc., 1996.
INC2209486, LIFESEQ™ Clone Information Results, Incyte Pharmaceuticals Inc., 1996.
INC1851527, LIFESEQ™ Clone Information Results, Incyte Pharmaceuticals Inc., 1996.
INC891710, LIFESEQ™ Clone Information Results, Incyte Pharmaceuticals Inc., 1996.
INC1329031, LIFESEQ™ Clone Information Results, Incyte Pharmaceuticals Inc., 1996.
Clone 1329031, LIFESEQ™ Electronic Northern Results, Incyte Pharmaceuticals Inc., 1996.
PANCNOT07, LIFESEQ™ Library Information Results, Incyte Pharmaceuticals Inc., 1996.
LUNGFET03, LIFESEQ™ Library Information Results, Incyte Pharmaceuticals Inc., 1996.
STOMTUT01, LIFESEQ™ Library Information Results, Incyte Pharmaceuticals Inc., 1996.
SINTFET03, LIFESEQ™ Library Information Results, Incyte Pharmaceuticals Inc., 1996.
Strausberg, Accession No. AA530994, Cancer Genome Anatomy Project, 1997.
INC3663175, LIFESEQ™ Clone Information Results, Incyte Pharmaceuticals Inc., 1997.
INC3666305, LIFESEQ™ Clone Information Results, Incyte Pharmaceuticals Inc., 1997.
INC3605169, LIFESEQ™ Clone Information Results, Incyte Pharmaceuticals Inc., 1997.
LUNGNOT30, LIFESEQ™ Library Information Results, Incyte Pharmaceuticals Inc., 1997.
PANCNOT16, LIFESEQ™ Library Information Results, Incyte Pharmaceuticals Inc., 1997.
Feighner et al., *Science* 284: 2184–2188, 1999.
Miller et al., *Peptides* 16: 11–18, 1995.
Peeters et al., *Peptides* 13: 1103–1107, 1992.

* cited by examiner

*Primary Examiner*—David S. Romeo
(74) *Attorney, Agent, or Firm*—Robyn Adams

(57) ABSTRACT

The present invention is directed to polynucleotides, peptides, variants, and uses thereof for a novel peptide fragment designated TML peptides. Binding of the peptide fragment has been shown in kidney and small intestine. The present invention further includes agonists, antagonists, variants, antibodies, host cells expressing the cDNA encoding the novel TML peptides and methods for increasing gastric motility and secretion of digestive proteins and hormones using the novel TML peptides.

11 Claims, No Drawings

SEQUENCE LISTING

```
<160> NUMBER OF SEQ ID NOS: 13

<210> SEQ ID NO 1
<211> LENGTH: 351
<212> TYPE: DNA
<213> ORGANISM: Homo sapiens
<220> FEATURE:
<221> NAME/KEY: CDS
<222> LOCATION: (1)...(351)

<400> SEQUENCE: 1 atg ccc tcc cca ggg acc gtc tgc agc ctc ctg ctc ctc ggc atg ctc      48
Met Pro Ser Pro Gly Thr Val Cys Ser Leu Leu Leu Leu Gly Met Leu
1               5                   10                  15 tgg ctg gac ttg gcc atg gca ggc tcc agc ttc ctg agc cct gaa cac      96
Trp Leu Asp Leu Ala Met Ala Gly Ser Ser Phe Leu Ser Pro Glu His
            20                  25                  30 cag aga gtc cag cag aga aag gag tcg aag aag cca cca gcc aag ctg     144
Gln Arg Val Gln Gln Arg Lys Glu Ser Lys Lys Pro Pro Ala Lys Leu
        35                  40                  45 cag ccc cga gct cta gca ggc tgg ctc cgc ccg gaa gat gga ggt caa     192
Gln Pro Arg Ala Leu Ala Gly Trp Leu Arg Pro Glu Asp Gly Gly Gln
    50                  55                  60 gca gaa ggg gca gag gat gaa ctg gaa gtc cgg ttc aac gcc ccc ttt     240
Ala Glu Gly Ala Glu Asp Glu Leu Glu Val Arg Phe Asn Ala Pro Phe
65                  70                  75                  80 gat gtt gga atc aag ctg tca ggg gtt cag tac cag cag cac agc cag     288
Asp Val Gly Ile Lys Leu Ser Gly Val Gln Tyr Gln Gln His Ser Gln
```

```
                            85                    90                    95
gcc ctg ggg aag ttt ctt cag gac atc ctc tgg gaa gag gcc aaa gag        336
Ala Leu Gly Lys Phe Leu Gln Asp Ile Leu Trp Glu Glu Ala Lys Glu
                100                   105                   110 gcc cca gcc gac aag                                                     351
Ala Pro Ala Asp Lys
        115

<210> SEQ ID NO 2
<211> LENGTH: 117
<212> TYPE: PRT
<213> ORGANISM: Homo sapiens

<400> SEQUENCE: 2

Met Pro Ser Pro Gly Thr Val Cys Ser Leu Leu Leu Leu Gly Met Leu
  1               5                  10                  15

Trp Leu Asp Leu Ala Met Ala Gly Ser Ser Phe Leu Ser Pro Glu His
                 20                  25                  30

Gln Arg Val Gln Gln Arg Lys Glu Ser Lys Lys Pro Pro Ala Lys Leu
             35                  40                  45

Gln Pro Arg Ala Leu Ala Gly Trp Leu Arg Pro Glu Asp Gly Gly Gln
     50                  55                  60

Ala Glu Gly Ala Glu Asp Glu Leu Glu Val Arg Phe Asn Ala Pro Phe
 65                  70                  75                  80

Asp Val Gly Ile Lys Leu Ser Gly Val Gln Tyr Gln Gln His Ser Gln
                 85                  90                  95

Ala Leu Gly Lys Phe Leu Gln Asp Ile Leu Trp Glu Glu Ala Lys Glu
                100                  105                  110

Ala Pro Ala Asp Lys
        115

<210> SEQ ID NO 3
<211> LENGTH: 546
<212> TYPE: DNA
<213> ORGANISM: Sus scrofa
<220> FEATURE:
<221> NAME/KEY: CDS
<222> LOCATION: (40)...(396)

<400> SEQUENCE: 3
gggcagagac acacacgcgc ccagttgtcc agctccagg atg gtg tcc cgc aag         54
                                            Met Val Ser Arg Lys
                                              1               5 gct gtg gtc gtc ctg ctg gtg gtg cac gca gct gcc atg ctg gcc tcc       102
Ala Val Val Val Leu Leu Val Val His Ala Ala Ala Met Leu Ala Ser
             10                  15                  20 cac acg gaa gcc ttt gtt ccc agc ttt acc tac ggg gaa ctt cag agg       150
His Thr Glu Ala Phe Val Pro Ser Phe Thr Tyr Gly Glu Leu Gln Arg
         25                  30                  35 atg cag gaa aag gag cgg aat aaa ggg caa aag aaa tcc ctg agt gtc       198
Met Gln Glu Lys Glu Arg Asn Lys Gly Gln Lys Lys Ser Leu Ser Val
     40                  45                  50 cag cag gcg tcg gag gag ctc ggc cct ctg gac ccc tcg gag ccc acg       246
Gln Gln Ala Ser Glu Glu Leu Gly Pro Leu Asp Pro Ser Glu Pro Thr
 55                  60                  65 aag gaa gaa gaa agg gtg gtt atc aag ctg ctc gcg cct gtg gac att       294
Lys Glu Glu Glu Arg Val Val Ile Lys Leu Leu Ala Pro Val Asp Ile
 70                  75                  80                  85 gga atc agg atg gac tcc agg cag ctg gaa aag tac cgg gcc acc ctg       342
Gly Ile Arg Met Asp Ser Arg Gln Leu Glu Lys Tyr Arg Ala Thr Leu
```

```
                            90                   95                  100
gaa agg ctg ctg ggc cag gcg ccg cag tcc acc cag aac cag aat gcc          390
Glu Arg Leu Leu Gly Gln Ala Pro Gln Ser Thr Gln Asn Gln Asn Ala
            105                 110                 115 gcc aag taacaggccg ctgggggaga aggaggacac agctcggacc ccctcccac            446
Ala Lys gcagggaggg cctagaaatc cgctgggctt ggaaggaaaa caccctctcc caaacagccc        506 tcagccccc tcccccagca ataaagcgt ggaaataggc                                546

<210> SEQ ID NO 4
<211> LENGTH: 119
<212> TYPE: PRT
<213> ORGANISM: Sus scrofa

<400> SEQUENCE: 4

Met Val Ser Arg Lys Ala Val Val Leu Leu Val Val His Ala Ala
 1               5                  10                  15

Ala Met Leu Ala Ser His Thr Glu Ala Phe Val Pro Ser Phe Thr Tyr
            20                  25                  30

Gly Glu Leu Gln Arg Met Gln Glu Lys Glu Arg Asn Lys Gly Gln Lys
        35                  40                  45

Lys Ser Leu Ser Val Gln Gln Ala Ser Glu Glu Leu Gly Pro Leu Asp
    50                  55                  60

Pro Ser Glu Pro Thr Lys Glu Glu Arg Val Val Ile Lys Leu Leu
65                  70                  75                  80

Ala Pro Val Asp Ile Gly Ile Arg Met Asp Ser Arg Gln Leu Glu Lys
                85                  90                  95

Tyr Arg Ala Thr Leu Glu Arg Leu Leu Gly Gln Ala Pro Gln Ser Thr
            100                 105                 110

Gln Asn Gln Asn Ala Ala Lys
        115

<210> SEQ ID NO 5
<211> LENGTH: 6
<212> TYPE: PRT
<213> ORGANISM: Artificial Sequence
<220> FEATURE:
<223> OTHER INFORMATION: Artificial peptide
<221> NAME/KEY: VARIANT
<222> LOCATION: (2)...(2)
<223> OTHER INFORMATION: Xaa is any amino acid
<221> NAME/KEY: VARIANT
<222> LOCATION: (5)...(5)
<223> OTHER INFORMATION: Xaa is any amino acid

<400> SEQUENCE: 5

Glu Xaa Gln Arg Xaa Gln
 1               5

<210> SEQ ID NO 6
<211> LENGTH: 7
<212> TYPE: PRT
<213> ORGANISM: Artificial Sequence
<220> FEATURE:
<223> OTHER INFORMATION: Artificial peptide
<221> NAME/KEY: VARIANT
<222> LOCATION: (3)...(3)
<223> OTHER INFORMATION: Xaa is any amino acid
<221> NAME/KEY: VARIANT
<222> LOCATION: (5)...(5)
<223> OTHER INFORMATION: Xaa is any amino acid

<400> SEQUENCE: 6
```

```
Ala Pro Xaa Asp Xaa Gly Ile
 1               5
```

<210> SEQ ID NO 7
<211> LENGTH: 40
<212> TYPE: DNA
<213> ORGANISM: Artificial Sequence
<220> FEATURE:
<223> OTHER INFORMATION: oligonucleotide

<400> SEQUENCE: 7
ttcttcgact cctttctctg ctggactctc tggtgttcag                    40

<210> SEQ ID NO 8
<211> LENGTH: 18
<212> TYPE: DNA
<213> ORGANISM: Artificial Sequence
<220> FEATURE:
<223> OTHER INFORMATION: OLIGONUCLEOTIDE

<400> SEQUENCE: 8
catgctctgg ctggactt                                           18

<210> SEQ ID NO 9
<211> LENGTH: 18
<212> TYPE: DNA
<213> ORGANISM: Artificial Sequence
<220> FEATURE:
<223> OTHER INFORMATION: OLIGONUCLEOTIDE

<400> SEQUENCE: 9
ctggactctc tggtgttc                                           18

<210> SEQ ID NO 10
<211> LENGTH: 54
<212> TYPE: DNA
<213> ORGANISM: Homo sapiens

<400> SEQUENCE: 10
ggctccagct tcctgagccc tgaacaccag agagtccagc agagaaagga gtcg    54

<210> SEQ ID NO 11
<211> LENGTH: 18
<212> TYPE: PRT
<213> ORGANISM: Homo sapiens

<400> SEQUENCE: 11

```
Gly Ser Ser Phe Leu Ser Pro Glu His Gln Arg Val Gln Gln Arg Lys
 1               5                  10                  15

Glu Ser
```

<210> SEQ ID NO 12
<211> LENGTH: 18
<212> TYPE: PRT
<213> ORGANISM: Artificial Sequence
<220> FEATURE:
<221> NAME/KEY: VARIANT
<222> LOCATION: (1)...(1)
<223> OTHER INFORMATION: Xaa is Gly, Ser, Ala, Thr, or Met
<221> NAME/KEY: VARIANT
<222> LOCATION: (2)...(2)
<223> OTHER INFORMATION: Xaa is Gly, Ser, Ala, Thr, or Met
<221> NAME/KEY: VARIANT
<222> LOCATION: (3)...(3)
<223> OTHER INFORMATION: Xaa is Gly, Ser, Ala, Thr, or Met
<221> NAME/KEY: VARIANT

```
<222> LOCATION: (4)...(4)
<223> OTHER INFORMATION: Xaa is Phe, Trp, Tyr, Leu, Val, or Ile
<221> NAME/KEY: VARIANT
<222> LOCATION: (5)...(5)
<223> OTHER INFORMATION: Xaa is Phe, Tyr, Leu, Val, or Ile
<221> NAME/KEY: VARIANT
<222> LOCATION: (6)...(6)
<223> OTHER INFORMATION: Xaa is Gly, Ser, Ala, Thr, Met, or Pro
<221> NAME/KEY: VARIANT
<222> LOCATION: (7)...(7)
<223> OTHER INFORMATION: Xaa is Gly, Pro, Ala, Ile, leu or Val
<221> NAME/KEY: VARIANT
<222> LOCATION: (8)...(8)
<223> OTHER INFORMATION: Xaa is Glu or Asp
<221> NAME/KEY: VARIANT
<222> LOCATION: (9)...(9)
<223> OTHER INFORMATION: Xaa is His, Arg, Lys, Phe, or Tyr
<221> NAME/KEY: VARIANT
<222> LOCATION: (10)...(10)
<223> OTHER INFORMATION: Xaa is Gln, Asn, Ser, Thr, His, Ala, Glu, Asp,
      Lys, or Arg
<221> NAME/KEY: VARIANT
<222> LOCATION: (11)...(11)
<223> OTHER INFORMATION: Xaa is Gln, Asn, Ser, Thr, His, Ala, Glu, Asp,
      Lys, or Arg
<221> NAME/KEY: VARIANT
<222> LOCATION: (12)...(12)
<223> OTHER INFORMATION: Xaa is Met, Val, Leu, Ile, Trp, or Phe
<221> NAME/KEY: VARIANT
<222> LOCATION: (13)...(13)
<223> OTHER INFORMATION: Xaa is Gln, Asn, Ser, Thr, His, Ala, Glu, Asp,
      Lys, or Arg
<221> NAME/KEY: VARIANT
<222> LOCATION: (14)...(14)
<223> OTHER INFORMATION: Xaa is Gln, Asn, Ser, Thr, His, Ala, Glu, Asp,
      Lys, or Arg
<221> NAME/KEY: VARIANT
<222> LOCATION: (15)...(15)
<223> OTHER INFORMATION: Xaa is Gln, Asn, Ser, Thr, His, Ala, Glu, Asp,
      Lys, or Arg
<221> NAME/KEY: VARIANT
<222> LOCATION: (16)...(16)
<223> OTHER INFORMATION: Xaa is Gln, Asn, Ser, Thr, His, Ala, Glu, Asp,
      Lys, or Arg
<221> NAME/KEY: VARIANT
<222> LOCATION: (17)...(17)
<223> OTHER INFORMATION: Xaa is Gln, Asn, Ser, Thr, His, Ala, Glu, Asp,
      Lys, or Arg
<221> NAME/KEY: VARIANT
<222> LOCATION: (18)...(18)
<223> OTHER INFORMATION: Xaa is Gln, Asn, Ser, Thr, His, Ala, Glu, Asp,
      Lys, or Arg

<400> SEQUENCE: 12

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 13
<211> LENGTH: 14
<212> TYPE: PRT
<213> ORGANISM: Artificial Sequence
<220> FEATURE:
<223> OTHER INFORMATION: Artificial peptide

<400> SEQUENCE: 13

Ser Leu Ser Arg Gln Gly Ser His Gln Phe Pro Gln Glu Val
1               5                   10
```

TML PEPTIDES

REFERENCE TO RELATED APPLICATIONS

This application claims benefit of Provisional Application No. 60/041,102, filed on Mar. 24, 1997 under 35 U.S.C. §119(e)(1). Additionally, this application is a continuation-in-part of application Ser. No. 09/046,479 filed on Mar. 23, 1998, U.S. Pat. No. 6,291,653, and claims benefit under 35 U.S.C 35 §120, from said patent.

BACKGROUND OF THE INVENTION

Many of the regulatory peptides that are important in maintaining nutritional homeostasis are found in the gastrointestinal environment. These peptides may be synthesized in the digestive system and act locally, but can also be identified in the brain as well. In addition, the reverse is also found, i.e., peptides are synthesized in the brain, but found to regulate cells in the gastrointestinal tract. This phenomena has been called the "brain-gut axis" and is important for signaling satiety, regulating body temperature and other physiological processes that require feedback between the brain and gut.

The gut peptide hormones include gastrin, cholecystokinin (CCK), secretin, gastric inhibitory peptide (GIP), vasoactive intestinal polypeptide (VIP), motilin, somatostatin, pancreatic peptide (PP), substance P and neuropeptide Y (NPY), and use several different mechanisms of action. For example, gastrin, motilin and CCK function as endocrine- and neurocrine-type hormones. Others, such as gastrin and GIP, are thought to act exclusively in an endocrine fashion. Other modes of action include a combination of endocrine, neurocrine and paracrine action (somatostatin); exclusively neurocrine action (NPY); and a combination of neurocrine and paracrine actions (VIP and Substance P). Most of the gut hormone actions are mediated by membrane-bound receptors and activate second messenger systems. For a review of gut peptides see, Mulvihill et al., in *Basic and Clinical Endocrinology*, pp.551–570, 4th edition Greenspan F. S. and Baxter, J. D. editors., Appleton & Lange: Norwalk, Conn., 1994.

Many of these gut peptides are synthesized as inactive precursor molecules that require multiple peptide cleavages to be activated. The family known as the "glucagon-secretin" family, which includes VIP, gastrin, secretin, motilin, glucagon and galanin, exemplifies peptides regulated by multiple cleavages and post-translational modifications.

Motilin is a 22 amino acid peptide found in gut tissue of mammalian species (Domschke, W., *Digestive Diseases* 22(5):454–461, 1977). The DNA and amino acid sequences for porcine prepromotilin have been identified (U.S. Pat. No. 5,006,469). Motilin has been characterized as a factor capable of increasing gastric motility, affecting the secretory function of the stomach by stimulating pepsin secretion (Brown et al., *Canadian J. of Physiol. Pharmacol.* 49:399–405, 1971), and recent evidence suggests a role in myoelectric regulation of stomach and small intestine. Cyclic increases of motilin have been correlated with phase III of the interdigestive myoelectric complex and the hunger contraction of the duodenum (Chey et al., in *Gut Hormones*, (eds.) Bloom, S. R., pp. 355–358, Edinburgh, Churchill Livingstone, 1978; Lee et al, *Am. J. Digestive Diseases*, 23:789–795, 1978; and Itoh et al.,*Am. J. Digestive Diseases*, 23:929–935, 1978). Motilin and analogues of motilin have been demonstrated to produce contraction of gastrointestinal smooth muscle, but not other types of smooth muscle cells (Strunz et al., *Gastroenterology* 68:1485–1491, 1975).

The present invention is directed to a novel peptide fragment, and the DNA segment encoding it, of a previously described secreted protein, zsig33 (Sheppard, P. O., WO98/42840:1998). The present invention is also directed to a limited number of variants of said peptide fragment. The discovery of this novel peptide fragment is important for further elucidation of the how the body maintains its nutritional homeostasis and development of therapeutics to intervene in those processes, as well as other uses that will be apparent from the teachings herein.

SUMMARY OF THE INVENTION

Within one apsect the present invention provides an isolated polynucleotide molecule encoding an isolated peptide molecule as shown in SEQ ID NO:12, said peptide molecule consisting of residues X through Y, wherein X is an integer from 1 to 4, inclusive, and wherein Y is 14 or 18, and wherein at least (Y minus X) minus 2 residues are as in the corresponding region of SEQ ID NO:11. Within one embodiment, the isolated peptide molecule has at least (Y minus X) minus 1 residues that are as in the corresponding region of SEQ ID NO:11. Within another embodiment, the isolated polypeptide molecule has at least (Y minus X) residues that are as in the corresponding region of SEQ ID NO:11. Within another embodiment, these isolated peptide molecule are provided. Methods for modulating contractility in duodenum or jejunum tissue and for modulating pancreatic secretion of hormones and digestive enzymes comprising administering these peptides are also provided.

Within another aspect, the present invention provides an isolated polynucleotide molecule encoding an isolated peptide molecule as shown in SEQ ID NO:12, said peptide molecule consisting of residues X through 11, wherein X is 1 or 2, and wherein at least (11 minus X) minus 2 residues are as in the corresponding region of SEQ ID NO:11. Within an embodiment, said peptide molecule has at least (11 minus X) minus 1 residues that are as in the corresponding region of SEQ ID NO:11. Within another embodiment, said polypeptide molecule has at least 11 minus X residues that are as in the corresponding region of SEQ ID NO:11. Within another embodiment, these isolated peptide molecules are provided. Methods of modulating contractility in duodenum or jejunum tissue and pancreatic secretion of hormones and digestive enzymes comprising administering said isolated polypeptide are also provided.

Within another aspect, the invention provides an isolated polynucleotide molecule encoding an isolated peptide molecule as shown in SEQ ID NO:12, said peptide molecule consisting of residues 1 through 10, and wherein at least seven residues are as in the corresponding region of SEQ ID NO:11. Within an embodiment, said isolated peptide has at least eight residues that are as in the corresponding region of SEQ ID NO:11 above. Within another embodiment, said isolated peptide has at least nine residues that are as in the corresponding region of SEQ ID NO:11. Within another embodiment, these isolated peptide molecules are provided. Methods for modulating contractility in duodenum or jejunum tissue, and for modulating pancreatic secretion of hormones and digestive enzymes comprising administering said isolated polypeptide to a mammal are also provided.

Within another aspect is provided an isolated polynucleotide molecule encoding an isolated peptide, wherein the peptide is selected from the group consisting of: a) residues 2 to 18 of SEQ ID NO:11; b) residues 2 to 14 of SEQ ID NO:11; c) residues 3 to 18 of SEQ ID NO:11; d) residues 3 to 14 of SEQ ID NO:11; e) residues 4 to 18 of SEQ ID NO:11; f) residues 4 to 14 of SEQ ID NO:11; g) residues 1 to 11 of SEQ ID NO:11; h) residues 1 to 10 of SEQ ID NO:11; and i) residues 2 to 11 of SEQ ID NO:11. Within an embodiment, the invention provides the isolated peptide molecule described herein. Within another aspect is provided a method of modulating contractility in duodenum or jejunum tissue comprising applying the isolated peptide to said tissue. Within another embodiment the invention provides a method of modulating pancreatic secretion of hormones and digestive enzymes comprising administering the isolated peptide to a mammal.

DETAILED DESCRIPTION OF THE INVENTION

Prior to describing the present invention in detail, it may be helpful to define certain terms used herein:

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, α-globin, β-globin, and myoglobin are paralogs of each other.

The term "allelic variant" denotes any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "expression vector" denotes a DNA molecule, linear or circular, that comprises a segment encoding a polypeptide of interest operably linked to additional segments that provide for its transcription. Such additional segments may include promoter and terminator sequences, and may optionally include one or more origins of replication, one or more selectable markers, an enhancer, a polyadenylation signal, and the like. Expression vectors are generally derived from plasmid or viral DNA, or may contain elements of both.

The term "isolated", when applied to a polynucleotide molecule, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985). When applied to a protein, the term "isolated" indicates that the protein is found in a condition other than its native environment, such as apart from blood and animal tissue. In a preferred form, the isolated protein is substantially free of other proteins, particularly other proteins of animal origin. It is preferred to provide the protein in a highly purified form, i.e., greater than 95% pure, more preferably greater than 99% pure.

The term "corresponding to", when applied to positions of amino acid residues in sequences, means corresponding positions in a plurality of sequences when the sequences are optimally aligned.

The term "operably linked", when referring to DNA segments, denotes that the segments are arranged so that they function in concert for their intended purposes, e.g. transcription initiates in the promoter and proceeds through the coding segment to the terminator.

The term "polynucleotide" denotes a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "complements of polynucleotide molecules" denotes polynucleotide molecules having a complementary base sequence and reverse orientation as compared to a reference sequence. For example, the sequence 5' ATG-CACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide) Degenerate codons contain different triplets of nucleotides, but encode the same amino acid residue (i.e., GAU and GAC triplets each encode Asp).

The term "promoter" denotes a portion of a gene containing DNA sequences that provide for the binding of RNA polymerase and initiation of transcription. Promoter sequences are commonly, but not always, found in the 5' non-coding regions of genes.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger peptide is commonly cleaved to remove the secretory peptide during transit through the secretory pathway.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. Most nuclear receptors also exhibit a multi-domain structure, including an amino-terminal, transactivating domain, a DNA binding domain and a ligand binding domain. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of <$10^9$ $M^{-1}$.

All references cited herein are incorporated by reference in their entirety.

The present invention is based in part upon the discovery of a novel peptide fragment of a previously described secreted polypeptide known as zsig33 (Sheppard, P. O., WO 98/42840). Zsig33 (shown in SEQ ID NO:s 1 and 2) which has homology to motilin has been found to be transcribed in the gastrointestinal system. The novel peptide fragments of the present invention have homology to the active peptide of motilin. The polynucleotide and polypeptide sequences for motilin are shown in SEQ ID NOs:3 and 4, respectively. The novel peptide fragments (shown in SEQ ID NO:11) have been designated Truncated Motilin-Like (TML) peptides and are also shown in Table A. Variants of this fragment are also described herein and shown in SEQ ID NO:12. Thus, residues 1 through 18 of SEQ ID NOs:11 and 12 correspond to residues 24 to 41 of SEQ ID NO:2. SEQ ID NO:10 shows the polynucleotide sequence encoding SEQ ID NO:11.

Motilin is member of a family of polypeptides that regulate the gastrointestinal physiology. The family of polypeptides important in gastrointestinal regulation to which motilin belongs includes glucagon, gastrin, galanin, and vasoactive intestinal peptide (VIP). These polypeptides are synthesized in a precursor form that requires multiple steps of processing to the active form. Particularly relevant to the peptide of the present invention are motilin, VIP and galanin, where processing involves removal of signal sequence, followed by cleavage of one or more accessory peptides to release the active peptide. The resulting active peptide is generally small (10–30 amino acids) and may require further post-translational modifications, such as amidation, sulfation or pyrrolidan carbonylic acid modification of glutamic residues.

Analysis of the tissue distribution of the mRNA corresponding to said secreted zsig33 protein showed that expression was highest in stomach, followed by apparent but decreased expression levels in small intestine and pancreas. The EST for the secreted zsig33 protein was derived from a pancreatic library, and has been shown in lung cDNA libraries. Thus, the novel TML peptide of SEQ ID NO:11 would be expected to localize to these tissues or to any other tissues accessible by the circulatory system of the body.

The active TML peptides are predicted to result from a C-terminal cleavage after amino acid residue 37 (Gln) or residue 41 (Ser) of SEQ ID NO: 2. However, many of the gut-brain peptides require multiple cleavages. For example, progastrin peptide is 101 amino acids, and is cleaved at the N-terminus resulting in sequentially smaller peptides (G34, G17 and G14) (Sugano et al., *J. Biol. Chem.* 260:11724–11729, 1985). Other peptides that require multiple processing steps include glucagon, for which C-terminal cleavages result in glucagon-like peptide 1 and glucagon-like peptide 2 and galanin, in which processing involves cleavage of a C-terminal peptide known as GMAP. Therefore, a peptide based on cleavage after amino acid 37 of SEQ ID NO: 2 (Gln) was synthesized and resulted in a 14 amino acid peptide with biological activity (from amino acid residue 24 (Gly) to amino acid residue 37 (Gln) of SEQ ID NO: 2).

Multiple signal peptidase cleavages are expected in the present invention. Thus, the amino terminal of the TML peptides may begin with glycine, residue 1 of SEQ ID NO:11, serine, residues 2 or 3 of SEQ ID NO:11 or phenylalanine, residue 4 of SEQ ID NO:11.

Dibasic peptide sites are often necessary to generate bioactive molecules in the gut-hormone peptide family. Such sites are present at residues 38 and 39 (Arg-Lys) and residues 42 and 43 (Lys-Lys) of SEQ ID NO:2. Thus, a protease (i.e., a metalloprotease, serine protease, aspartic protease, or cysteine protease) which is important for the activation of zsig33 cleaves the zsig33 polypeptide after these dibasic sites resulting in peptides which terminate in residues 39 or 43 of SEQ ID NO:2. (Cleavages can also occur after monobasic amino acids or other sites as well.) Carboxy-peptidases are likely to remove one or more residues from the carboxyl terminal of the active peptides. Thus, the processing of the active peptides by proteases and carboxy-peptidases result in the active zsig33 peptides which terminate in residue 37 (Glu) or 41 (Ser) of SEQ ID NO:2. These positions correspond to residues 14 and 18, respectively, of SEQ ID NO:11.

Based on analysis of the motilin family, residues 4 to 9 of SEQ ID NO:11 will be essential for receptor binding and activation. (Miller, P. et al., *Peptides* 16(1):11–18, 1995; and Peeters, T. L. et al,. *Peptides* 13(6):1103–1107, 1992). It should be noted that serine (residue 29 of SEQ ID NO:4) has been shown to be an isoleucine by Schubert, H. et al., *Can. J. Biochem.* 52:7–8, 1974. Furthermore, this analysis suggests that residues 4 (Phe), 5 (Leu), 6 (Ser) and 9 (His) of SEQ ID NO:11 are particularly important residues for receptor binding and/or activity.

Substitutions of residues within this six residue peptide, can result in variants with altered affinity of the peptide for the receptor or altered activation of the receptor. Such alterations can result in agonistic as well as antagonistic activity.

Additional substitutions of residues of TML peptides are further described herein. Conservative amino acid substitutions of certain residues between residues 4 (Phe) and residue 14 (Gln) of SEQ ID NO:11 result in variants which are potential antagonists. These variants will bind the receptor with high affinity, but cause low receptor activation. Preferably these positions are at residues 4 (Phe), 5 (Leu), 7 (Pro), and 9 (His) of SEQ ID NO:11.

Substitutions of residues in TML peptides may also result in variants which are agonists. Such substitutions may be based on conservative amino acid substitutions as in Table 2, or based on predictions made by comparison to the active peptide of motilin. These substitutions include positions 4 (Phe), 5 (Leu), and 9 (His) of SEQ ID NO:11. It is predicted, for example, that residue 4 (Phe) of SEQ ID NO:11 can be substituted with leucine, valine, or isoleucine; residue 5 (Leu) of SEQ ID NO:11 can be substituted with phenylalanine, valine, tyrosine or isoleucine; and that residue 9 (His) of SEQ ID NO:11 can be substituted with phenylalanine, or lysine. Similarly, residue 7 (Pro) of SEQ ID NO:11 can be substituted with alanine, glycine, isoleucine, valine, or leucine.

Additionally, there are positions of TML peptides at which mutations are not predicted to result in alteration of the binding affinity or activation of the receptor upon binding these mutants. These positions include, for example, residue 6 (Ser) of SEQ ID NO:11, at which substitution with alanine, proline, threonine, or glycine is not predicted to alter the binding of the mutant, or variants, as compared to wild-type zsig33.

Miller, P. et al., ibid., suggests that residues 33 (Gly) and 34 (Glu) of motilin (SEQ ID NO:4) form a transition region, and that residues 35 (Leu) to 47 (Gln) of motilin (SEQ ID NO:4) form an alpha helix which stabilizes the interactions of the receptor binding portion of motilin (residues 26 to 32 of SEQ ID NO:4) to its receptor. Similarly, the helical region, residues 10 (Gln) to residue 18 (Ser) of TML peptides (SEQ ID NO:11), can be substituted with residues that will to maintain the hydrophobic, hydrophilic and electrostatic nature required for forming a helix. Thus, amino acids at positions 10, 11, 13, 14, 15, 16, 17, and 18 of TML peptides can be glutamine, asparagine, serine, threonine, histidine, alanine, glutamic acid, aspartic acid, lysine, or arginine. Amino acids at position 12 of TML peptides can be methionine, leucine, valine, isoleucine, tryptophan, and phenylalanine. These substitutions will maintain the helical conformation and presentation of the binding site of the ligand to the receptor. TML peptides can be produced by in vitro or in vivo expression as well as chemical synthesis.

A receptor for motilin has been identified in the gastrointestinal system (Feighner, S. D. et al., Science 284:2184–8, 1999). Two forms of the motilin receptor (GPR38-A, and GPR38-B) were shown resulting from alternative splicing events. The TML receptor is likely to be a member of this seven transmembrane G protein-coupled receptor homolog class. Receptors in this class can be used for screening variants of TML peptides for binding and activity. Members of this receptor class appear to activate the phospholipase C signal transduction pathway. Hence, variants of TML peptides can also be tested using an assay that measures phospholipase C transduction. An exemplary assay of this sort measures release of $Ca^{2+}$ with aequorin, a bioluminescent $Ca^{2+}$-sensitive reporter protein. This assay is further described by Feighner, S. D. et al., ibid.

Critical carboxyl-terminal residues of motilin have been identified by Feighner, S. D. et al., ibid. If motilin is truncated with these residues, there is a sharp decrease in receptor binding and activity. These positions are residues 36 (Gln), and residue 37 (Arg) of motilin as shown in SEQ ID NO:4. An analysis of the amino acid sequence of TML peptides shows that residues 10 (Gln) and 11 (Arg) of SEQ ID NO:11 correspond to residues 36 and 37 of motilin, SEQ ID NO:4. Thus, TML peptides may have conservative amino acid substitutions at these positions. These specific substitutions are listed in Table A.

Binding studies have suggested that rabbit motilin binds to two populations of receptors with varying affinities (Poitras, P., Peptides 17:701–707, 1996) suggesting that there are two forms of motilin binding these receptors. One such receptor is located in the neural cells of the antrum, and the second receptor is located in the smooth muscle cells of the duodenum. Similarly, there may be more than one receptor which binds the TML ligand, or variants thereof, and the binding affinities may vary. Thus, the binding of TML peptides to its receptor(s) may result in different and varying biological events depending on the form of the TML peptide and the specific receptor-type to which it binds.

Based on a comparison of the residues of TML peptides to the residues of motilin which are known to be involved in binding the motilin receptor, there are predicted to be variants of the fragment peptide between residues 1 to 11 of SEQ ID NO:11 which have increased receptor affinity or activation.

Table A describes the possible substitutions for all variants of TML peptides. Variant peptides of TML peptides may have more than one substitution. A variant peptide having eighteen or fewer amino acids has preferably three or fewer amino acid substitutions; more preferably two or fewer amino acid substitutions; most preferably one amino acid substitution.

TABLE A

Peptide Substitutions

| Residue in SEQ ID NO:2 | Residue in SEQ ID NO:11 | Wild-Type Residue | Residue Substitutions listed in SEQ ID NO:12 |
|---|---|---|---|
| 24 | 1 | Gly | Ser, Ala, Thr, Met |
| 25 | 2 | Ser | Gly, Ala, Thr, Met |
| 26 | 3 | Ser | Gly, Ala, Thr, Met |
| 27 | 4 | Phe | Trp, Tyr, Leu, Val, Ile |
| 28 | 5 | Leu | Ile, Val, Phe, Tyr |
| 29 | 6 | Ser | Gly, Ala, Thr, Met, Pro |
| 30 | 7 | Pro | Ala, Gly, Ile, Leu, Val |
| 31 | 8 | Glu | Asp |
| 32 | 9 | His | Arg, Lys, Phe, Tyr |
| 33 | 10 | Gln | Asn, Ser, Thr, His, Ala, Glu, Asp, Lys, Arg |
| 34 | 11 | Arg | Gln, Asn, Ser, Thr, His, Ala, Glu, Asp, Lys, |
| 35 | 12 | Val | Met, Leu, Ile, Trp, Phe |
| 36 | 13 | Gln | Asn, Ser, Thr, His, Ala, Glu, Asp, Lys, Arg |
| 37 | 14 | Gln | Asn, Ser, Thr, His, Ala, Glu, Asp, Lys, Arg |
| 38 | 15 | Arg | Asn, Ser, Thr, His, Ala, Glu, Asp, Lys, Gln |
| 39 | 16 | Lys | Asn, Ser, Thr, His, Ala, Glu, Asp, Gln, Arg |
| 40 | 17 | Glu | Asn, Ser, Thr, His, Ala, Gln, Asp, Lys, Arg |
| 41 | 18 | Ser | Asn, Gln, Thr, His, Ala, Glu, Asp, Lys, Arg |

The present invention includes the following active TML peptides: residue 1 to residue 18; residue 1 to residue 14; residue 2 to residue 18; residue 2 to residue 14; residue 3 to residue 18; residue 3 to residue 14; residue 4 to residue 18; residue 4 to residue 14; residue 1 to residue 10; residue 1 to residue 11; and residue 2 to residue 11; all of SEQ ID NO:12.

The TML peptides can modulate the absorption of glucose. Factors affecting this modulation can include secretion of digestive enzymes or hormones in organs and tissues involved in the gastrointestinal tract. An assay to measure the absorption of glucose is shown in Example 4.

The C-terminal peptide (amino acid 42 to 117 of SEQ ID NO: 2) likely has some specialized activity as well. Processing of the active peptide for motilin (shown in SEQ ID NO: 4) results in a release of a C-terminal peptide of 70 amino acids, amino acid residue 50 (Ser) of SEQ ID NO:4 to amino acid residue 119 (Lys) of SEQ ID NO:4, known as motilin-associated peptide (MAP). Adelman et al., (U.S. Pat. No. 5,006,469) have postulated that MAP plays a role in regulation of digestion, appetite and nutrient absorption.

The highly conserved amino acids in the polypeptide zsig33 can be used as a tool to identify new family members. For instance, reverse transcription-polymerase chain reaction (RT-PCR) can be used to amplify sequences encoding the conserved motif from RNA obtained from a variety of tissue sources. Two such conserved domains have been identified using sequences from the present invention. The first domain is found at amino acid residues 31 to 36 of SEQ ID NO: 2, wherein the motif identified is Glu Xaa Gln Arg Xaa Gln, wherein Xaa is any amino acid residue (shown in SEQ ID NO: 5), and the second domain is found at amino acid residues 78 to 84 of SEQ ID NO: 2, wherein the motif identified is Ala Pro Xaa Asp Xaa Gly Ile, wherein Xaa is any amino acid residue (shown in SEQ ID NO: 6). In particular, highly degenerate primers designed from these sequences are useful for this purpose.

Those skilled in the art will readily recognize that, in view of the degeneracy of the genetic code, considerable sequence variation is possible among these polynucleotide molecules encoding SEQ ID NO:11, including all RNA sequences by substituting U for T. Thus, TML peptide-encoding polynucleotides and their RNA equivalents are contemplated by the present invention. Table 1 sets forth the one-letter codes used to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 1

| Nucleotide | Resolution | Nucleotide | Complement |
| --- | --- | --- | --- |
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons encompassing all possible codons for a given amino acid are set forth in Table 2.

TABLE 2

| Amino Acid | One Letter Code | Codons | Degenerate Codon |
| --- | --- | --- | --- |
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:11. Variant sequences can be readily tested for functionality as described herein.

Within preferred embodiments of the invention the isolated polynucleotides will hybridize to similar sized regions of SEQ ID NO:10, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is at least about 0.02 M at pH 7 and the temperature is at least about 60° C.

As previously noted, the isolated polynucleotides of the present invention include DNA and RNA. Methods for isolating DNA and RNA are well known in the art. It is generally preferred to isolate RNA from stomach, although DNA can also be prepared using RNA from other tissues or isolated as genomic DNA. Total RNA can be prepared using guanidine HCl extraction followed by isolation by centrifugation in a CsCl gradient (Chirgwin et al., *Biochemistry* 18:52–94, 1979). Poly $(A)^+$ RNA is prepared from total RNA using the method of Aviv and Leder (*Proc. Natl. Acad. Sci. USA* 69:1408–1412, 1972). Complementary DNA (CDNA) is prepared from poly$(A)^+$ RNA using known methods. Polynucleotides encoding TML peptides are then identified and isolated by, for example, hybridization or PCR.

The present invention further provides counterpart peptides and polynucleotides from other species (orthologs). of particular interest are TML peptides from other mammalian species, including murine, rat, porcine, ovine, bovine, canine, feline, equine and other primate proteins. Orthologs of the human proteins can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue of cell line. A TML ortholog-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to TML peptides Similar techniques can also be applied to the isolation of genomic clones.

Those skilled in the art will recognize that the sequence disclosed in SEQ ID NO: 10, and peptide encoded thereby, represents a single allele of the human TML peptide gene and peptide, and that allelic variation and alternative splicing are expected to occur. Allelic variants can be cloned by probing cDNA or genomic libraries from different individuals according to standard procedures. Allelic variants of the DNA sequence shown in SEQ ID NO: 10, including those containing silent mutations and those in which mutations result in amino acid sequence changes, are within the scope of the present invention, as are proteins which are the product of allelic variation of SEQ ID NO: 11.

The present invention also provides isolated TML peptides that are substantially homologous to the peptides of SEQ ID NO: 11 and their orthologs. The term "substantially homologous" is used herein to denote peptides having at least 80%, sequence identity to the sequences shown in SEQ ID NO: 11 or their orthologs. Such peptides will more preferably be at least 90% identical, and most preferably 95% or more identical to SEQ ID NO: 11 or its orthologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes).

(Smith and Johnson, *Gene* 67:31, 1988), maltose binding protein (Kellerman and Ferenci, *Methods Enzymol.* 90:459–463, 1982; Guan et al., *Gene* 67:21–30, 1987), thioredoxin, ubiquitin, cellulose binding protein, T7 polymerase, or other antigenic epitope or binding domain. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

TABLE 4

| Conservative amino acid substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

Sequence identity of polynucleotide molecules is determined by similar methods using a ratio as disclosed above.

Substantially homologous proteins and peptides are characterized as having one or more amino acid substitutions, deletions or additions. These changes are preferably of a minor nature, that is conservative amino acid substitutions (see Table 4) and other substitutions that do not significantly affect the folding or activity of peptide; small deletions, typically of one to about 30 amino acids; and amino- or carboxyl-terminal extensions, such as an amino-terminal methionine residue, a small linker peptide of up to about 20–25 residues, or a small extension that facilitates purification (an affinity tag), such as a poly-histidine tract, protein A (Nilsson et al., *EMBO J.* 4:1075, 1985; Nilsson et al., *Methods Enzymol.* 198:3, 1991), glutathione S transferase TABLE 4-continued

| Conservative amino acid substitutions | |
|---|---|
| Small: | glycine |
| | alanine |
| | serine |
| | threonine |
| | methionine |

In addition to the 20 standard amino acids, non-standard amino acids (such as 4-hydroxyproline, 6-N-methyl lysine, 2-aminoisobutyric acid, isovaline and α-methyl serine) may be substituted for amino acid residues of zsig33. A limited number of non-conservative amino acids, amino acids that are not encoded by the genetic code, and unnatural amino acids may be substituted for TML peptide amino acid residues. "Unnatural amino acids" have been modified after protein synthesis, and/or have a chemical structure in their side chain(s) different from that of the standard amino acids. Unnatural amino acids can be chemically synthesized, or preferably, are commercially available, and include pipecolic acid, thiazolidine carboxylic acid, dehydroproline, 3- and 4-methylproline, and 3,3-dimethylproline.

Essential amino acids in the TML peptides of the present invention can be identified according to procedures known in the art, such as site-directed mutagenesis or alanine-scanning mutagenesis (Cunningham and Wells, *Science* 244: 1081–1085, 1989). In the latter technique, single alanine mutations are introduced at every residue in the molecule, and the resultant mutant molecules are tested for biological activity (e.g., stimulation of gastrointestinal contractility, modulation of nutrient uptake, modulation of the secretion of digestive enzymes and hormones, modulation of secretion of enzymes and/or hormones in the pancreas, binding a TML/zsig33 receptor, or binding an antibody that specifically binds to residues 1 to 14 of SEQ ID NO:11) to identify amino acid residues that are critical to the activity of the molecule. See also, Hilton et al., *J. Biol. Chem.* 271:4699–4708, 1996. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related members of the glucagon-secretin family of gut-brain peptide hormones.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 46:145, 1986; Ner et al., *DNA* 7:127, 1988).

Mutagenesis methods as disclosed above can be combined with high-throughput, automated screening methods to detect activity of cloned, mutagenized polypeptides in host cells. Mutagenized DNA molecules that encode active peptides or polypeptides (e.g., stimulation of gastrointestinal contractility, modulation of nutrient uptake, modulation of the secretion of digestive enzymes and hormones, modulation of secretion of enzymes and/or hormones in the pancreas, binding a TML/zsig33 receptor, or binding an antibody that specifically binds to residues 1 to 14 of SEQ ID NO:11) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can identify and/or prepare a variety of peptides that are substantially homologous to residues 1 to 18 of SEQ ID NO: 11 or allelic variants thereof and retain properties of the wild-type protein. Such peptides may also include additional polypeptide segments as generally disclosed above.

The peptides of the present invention, including full-length proteins and fragments thereof, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al. (eds.), *Current Protocols in Molecular Biology*, John Wiley and Sons, Inc., NY, 1987, which are incorporated herein by reference.

In general, a DNA sequence encoding a TML peptide of the present invention is operably linked to other genetic elements required for its expression, generally including a transcription promoter and terminator within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct the export of TML peptides, or variants thereof, from the host cell, a DNA segment for a TML peptide, or variant thereof, is linked to a second DNA segment encoding a secretory peptide (i.e., a secretory signal sequence, also known as a leader sequence, prepro sequence of pre-sequence). The secretory signal sequence may be that of the native zsig33 polypeptide, i.e., residues 1 to 23 of SEQ ID NO:2, or may be derived from another secreted protein (e.g., t-PA) or synthesized de novo. The secretory signal sequence is joined to the TML DNA sequence in the correct reading frame. Secretory signal sequences are commonly positioned 5' to the DNA sequence encoding the propeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are also preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology*, John Wiley and Sons, Inc., NY, 1987), liposome-mediated transfection (Hawley-Nelson et al., *Focus* 15:73, 1993; Ciccarone et al., *Focus* 15:80, 1993), and viral vectors (A. Miller and G. Rosman, *BioTechniques* 7:980–90, 1989; Q. Wang and M. Finer, *Nature Med.* 2:714–16, 1996), which are incorporated herein by reference. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g., hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci. (Bangalore)* 11:47–58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). DNA encoding the TML peptide is inserted into the baculoviral genome in place of the AcNPV polyhedrin gene coding sequence by one of two methods. The first is the traditional method of homologous DNA recombination between wild-type AcNPV and a transfer vector containing the TML peptide gene flanked by AcNPV sequences. Suitable insect cells, e.g. SF9 cells, are infected with wild-type AcNPV and transfected with a transfer vector comprising a polynucleotide for TML peptides operably linked to an AcNPV polyhedrin gene promoter, terminator, and flanking sequences. See, King, L. A. and Possee, R. D., *The Baculovirus Expression System: A Laboratory Guide,* London, Chapman & Hall; O'Reilly, D. R. et al., *Baculovirus Expression Vectors: A Laboratory Manual,* New York, Oxford University Press., 1994; and, Richardson, C. D., Ed., *Baculovirus Expression Protocols. Methods in Molecular Biology,* Totowa, N.J., Humana Press, 1995. Natural recombination within an insect cell will result in a recombinant baculovirus which contains TML driven by the polyhedrin promoter. Recombinant viral stocks are made by methods commonly used in the art.

The second method of making recombinant baculovirus utilizes a transposon-based system described by Luckow (Luckow, V. A, et al., *J Virol* 67:4566–79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the TML peptide into a baculovirus genome maintained in *E. coli* as a large plasmid called a "bacmid." The pFastBac1™ transfer vector utilizes the AcNPV polyhedrin promoter to drive the expression of the gene of interest, in this case TML. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J Gen Virol* 71:971–6, 1990; Bonning, B. C. et al., *J Gen Virol* 75:1551–6, 1994; and, Chazenbalk, G. D., and Rapoport, B., *J Biol Chem* 270:1543–9, 1995. In such transfer vector constructs, a short or long version of the basic protein promoter can be used. Moreover, transfer vectors can be constructed which replace the native zsig33 secretory signal sequences (i.e., residues 1 to 23 of SEQ ID NO:2) with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zsig33 secretory signal sequence. In addition, transfer vectors can include an in-frame fusion with DNA encoding an epitope tag at the C- or N-terminus of the expressed TML peptide, for example, a Glu-Glu epitope tag (Grussenmeyer, T. et al., *Proc Natl Acad Sci.* 82:7952–4, 1985). Using a technique known in the art, a transfer vector containing TML polynucleotides is transformed into *E. Coli,* and screened for bacmids which contain an interrupted lacZ gene indicative of recombinant baculovirus. The bacmid DNA containing the recombinant baculovirus genome is isolated, using common techniques, and used to transfect Spodoptera frugiperda cells, e.g. Sf9 cells. Recombinant virus that expresses TML peptides are subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA,* ASM Press, Washington, D.C., 1994. Another suitable cell line is the High FiveO™ cell line (Invitrogen) derived from *Trichoplusia ni* (U.S. Pat. No. 5,300,435). Commercially available serum-free media are used to grow and maintain the cells. Suitable media are Sf900 II™ (Life Technologies) or ESF 921™ (Expression Systems) for the Sf9 cells; and Ex-cellO405™ (JRH Biosciences, Lenexa, Kans.) or Express FiveO™ (Life Technologies) for the *T. ni* cells. The cells are grown up from an inoculation density of approximately $2-5 \times 10^5$ cells to a density of $1-2 \times 10^6$ cells at which time a recombinant viral stock is added at a multiplicity of infection (MOI) of 0.1 to 10, more typically near 3. The recombinant virus-infected cells typically produce the recombinant TML peptide at 12–72 hours post-infection and secrete it with varying efficiency into the medium. The culture is usually harvested 48 hours post-infection. Centrifugation is used to separate the cells from the medium (supernatant). The supernatant containing the TML peptide is filtered through micropore filters, usually 0.45 μm pore size. Procedures used are generally described in available laboratory manuals (King, L. A. and Possee, R. D., ibid.; O'Reilly, D. R. et al., ibid.; Richardson, C. D., ibid.). Subsequent purification of the TML peptide from the supernatant can be achieved using methods described herein.

Fungal cells, including yeast cells, and particularly cells of the genera Saccharomyces and Pichia, can also be used within the present invention, such as for producing TML peptides or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii, Pichia methanolica* and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco-Laboratories), 0.004% adenine and 0.006% L-leucine).

Expressed recombinant TML peptides can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable anion exchange media include derivatized dextrans, agarose, cellulose, polyacrylamide, specialty silicas, and the like. PEI, DEAE, QAE and Q derivatives are preferred, with DEAE Fast-Flow Sepharose (Pharmacia, Piscataway, N.J.) being particularly preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods,* Pharmacia LKB Biotechnology, Uppsala, Sweden, 1988.

To facilitate purification of the secreted peptide, a C-terminal extension, such as a poly-histidine tag, substance P, Flag peptide (Hopp et al., *Bio/Technology* 6:1204–1210, 1988; available from Eastman Kodak Co., New Haven, Conn.) or another polypeptide or protein for which an antibody or other specific binding agent is available, can be fused to the TML peptide.

The peptides and variants of the present invention can be isolated by exploitation of small size and low pI. For example, peptides and variants of the present invention can be bound to anionic exchanges at low pH values. Other methods of purification include purification of glycosylated proteins by lectin affinity chromatography and ion exchange chromatography (*Methods in Enzymol.,* Vol. 182, "Guide to Protein Purification", M. Deutscher, (ed.), Acad. Press, San Diego, 1990, pp.529–39). Alternatively, a fusion of the peptide or variant of interest and an affinity tag (e.g., polyhistidine, maltose-binding protein, an immunoglobulin domain) may be constructed to facilitate purification.

Polypeptide fusions of the present invention will generally contain not more than about 1,500 amino acid residues, preferably not more than about 1,200 residues, more preferably not more than about 1,000 residues, and will in many cases be considerably smaller. For example, residues of TML peptides can be fused to *E. coli* b-galactosidase (1,021 residues; see Casadaban et al., *J. Bacteriol.* 143:971–980, 1980), a 10-residue spacer, and a 4-residue factor Xa cleavage site. In a second example, residues of a TML peptide can be fused to maltose binding protein (approximately 370 residues), a 4-residue cleavage site, and a 6-residue polyhistidine tag.

Protein refolding (and optionally reoxidation) procedures may be advantageously used. It is preferred to purify the protein to >80% purity, more preferably to >90% purity, even more preferably >95%, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

TML peptides, variants and or fragments thereof may also be prepared through chemical synthesis. TML peptides may be monomers or multimers; glycosylated or non-glycosylated; pegylated or non-pegylated; amidated or non-amidated; sulfated or non-sulfated; and may or may not include an initial methionine amino acid residue. For example, TML peptides can also be synthesized by exclusive solid phase synthesis, partial solid phase methods, fragment condensation or classical solution synthesis. The peptides are preferably prepared by solid phase peptide synthesis, for example as described by Merrifield, *J. Am. Chem. Soc.* 85:2149, 1963. The synthesis is carried out with amino acids that are protected at the alpha-amino terminus. Trifunctional amino acids with labile side-chains are also protected with suitable groups to prevent undesired chemical reactions from occurring during the assembly of the polypeptides. The alpha-amino protecting group is selectively removed to allow subsequent reaction to take place at the amino-terminus. The conditions for the removal of the alpha-amino protecting group do not remove the side-chain protecting groups.

The alpha-amino protecting groups are those known to be useful in the art of stepwise polypeptide synthesis. Included are acyl type protecting groups (e.g., formyl, trifluoroacetyl, acetyl), aryl type protecting groups (e.g., biotinyl), aromatic urethane type protecting groups [e.g., benzyloxycarbonyl (Cbz), substituted benzyloxycarbonyl and 9-fluorenylmethyloxycarbonyl (Fmoc)], aliphatic urethane protecting groups [e.g., t-butyloxycarbonyl (tBoc), isopropyloxycarbonyl, cyclohexloxycarbonyl] and alkyl type protecting groups (e.g., benzyl, triphenylmethyl). The preferred protecting groups are tBoc and Fmoc.

The side-chain protecting groups selected must remain intact during coupling and not be removed during the deprotection of the amino-terminus protecting group or during coupling conditions. The side-chain protecting groups must also be removable upon the completion of synthesis using reaction conditions that will not alter the finished polypeptide. In tBoc chemistry, the side-chain protecting groups for trifunctional amino acids are mostly benzyl based. In Fmoc chemistry, they are mostly tert-butyl or trityl based.

In tBoc chemistry, the preferred side-chain protecting groups are tosyl for arginine, cyclohexyl for aspartic acid, 4-methylbenzyl (and acetamidomethyl) for cysteine, benzyl for glutamic acid, serine and threonine, benzyloxymethyl (and dinitrophenyl) for histidine, 2-Cl-benzyloxycarbonyl for lysine, formyl for tryptophan and 2-bromobenzyl for tyrosine. In Fmoc chemistry, the preferred side-chain protecting groups are 2,2,5,7,8-pentamethylchroman-6-sulfonyl (Pmc) or 2,2,4,6,7-pentamethyldihydrobenzofuran-5-sulfonyl (Pbf) for arginine, trityl for asparagine, cysteine, glutamine and histidine, tert-butyl for aspartic acid, glutamic acid, serine, threonine and tyrosine, tBoc for lysine and tryptophan.

For the synthesis of phosphopeptides, either direct or post-assembly incorporation of the phosphate group is used. In the direct incorporation strategy, the phosphate group on serine, threonine or tyrosine may be protected by methyl, benzyl, or tert-butyl in Fmoc chemistry or by methyl, benzyl or phenyl in tBoc chemistry. Direct incorporation of phosphotyrosine without phosphate protection can also be used in Fmoc chemistry. In the post-assembly incorporation strategy, the unprotected hydroxyl groups of serine, threonine or tyrosine are derivatized on solid phase with di-tert-butyl-, dibenzyl- or dimethyl-N,N'-diisopropylphosphoramidite and then oxidized by tert-butylhydroperoxide.

Solid phase synthesis is usually carried out from the carboxyl-terminus by coupling the alpha-amino protected (side-chain protected) amino acid to a suitable solid support. An ester linkage is formed when the attachment is made to a chloromethyl, chlortrityl or hydroxymethyl resin, and the resulting polypeptide will have a free carboxyl group at the C-terminus. Alternatively, when an amide resin such as benzhydrylamine or p-methylbenzhydrylamine resin (for tboc chemistry) and Rink amide or PAL resin (for Fmoc chemistry) are used, an amide bond is formed and the resulting polypeptide will have a carboxamide group at the C-terminus. These resins, whether polystyrene- or polyamide-based or polyethyleneglycol-grafted, with or without a handle or linker, with or without the first amino acid attached, are commercially available, and their preparations have been described by Stewart et al., "Solid Phase Peptide Synthesis" (2nd Edition), (Pierce Chemical Co., Rockford, Ill., 1984) and Bayer & Rapp Chem. Pept. Prot. 3:3 (1986); and Atherton et al., Solid Phase Peptide Synthesis: *A Practical Approach*, IRL Press, Oxford, 1989.

The C-terminal amino acid, protected at the side chain if necessary, and at the alpha-amino group, is attached to a hydroxylmethyl resin using various activating agents including dicyclohexylcarbodiimide (DCC), N,N'-diisopropylcarbodiimide (DIPCDI) and carbonyldiimidazole (CDI). It can be attached to chloromethyl or chlorotrityl resin directly in its cesium tetramethylammonium salt form or in the presence of triethylamine (TEA) or diisopropylethylamine (DIEA). First amino acid attachment to an amide resin is the same as amide bond formation during coupling reactions.

Following the attachment to the resin support, the alpha-amino protecting group is removed using various reagents depending on the protecting chemistry (e.g., tBoc, Fmoc). The extent of Fmoc removal can be monitored at 300–320 nm or by a conductivity cell. After removal of the alpha-amino protecting group, the remaining protected amino acids are coupled stepwise in the required order to obtain the desired sequence.

Various activating agents can be used for the coupling reactions including DCC, DIPCDI, 2-chloro-1,3-dimethylimidium hexafluorophosphate (CIP), benzotriazol-1-yl-oxy-tris-(dimethylamino)-phosphonium hexafluorophosphate (BOP) and its pyrrolidine analog (PyBOP), bromo-tris-pyrrolidino-phosphonium hexafluorophosphate (PyBroP), O-(benzotriazol-1-yl)-1,1,3,3-tetramethyluronium hexafluorophosphate (HBTU) and its tetrafluoroborate analog (TBTU) or its pyrrolidine analog (HBPyU), O-(7-azabenzotriazol-1-yl)-1,1,3,3-tetramethyl-uronium hexafluorophosphate (HATU) and its tetrafluoroborate analog (TATU) or its pyrrolidine analog (HAPyU). The most common catalytic additives used in coupling reactions include 4-dimethylaminopyridine (DMAP), 3-hydroxy-3,4-dihydro-4-oxo-1,2,3-benzotriazine (HODhbt), N-hydroxybenzotriazole (HOBt) and 1-hydroxy-7-azabenzotriazole (HOAt). Each protected amino acid is used in excess (>2.0 equivalents), and the couplings are usually carried out in N-methylpyrrolidone (NMP) or in DMF, CH2Cl2 or mixtures thereof. The extent of completion of the coupling reaction can be monitored at each stage, e.g., by the ninhydrin reaction as described by Kaiser et al., *Anal. Biochem.* 34:595, 1970.

After the entire assembly of the desired peptide, the peptide-resin is cleaved with a reagent with proper scavengers. The Fmoc peptides are usually cleaved and deprotected by TFA with scavengers (e.g., H2O, ethanedithiol, phenol and thioanisole). The tBoc peptides are usually cleaved and deprotected with liquid HF for 1–2 hours at −5 to 0° C., which cleaves the polypeptide from the resin and removes most of the side-chain protecting groups. Scavengers such as anisole, dimethylsulfide and p-thiocresol are usually used with the liquid HF to prevent cations formed during the cleavage from alkylating and acylating the amino acid residues present in the polypeptide. The formyl group of tryptophan and the dinitrophenyl group of histidine need to be removed, respectively by piperidine and thiophenyl in DMF prior to the HF cleavage. The acetamidomethyl group of cysteine can be removed by mercury(II)acetate and alternatively by iodine, thallium(III)trifluoroacetate or silver tetrafluoroborate which simultaneously oxidize cysteine to cystine. Other strong acids used for tBoc peptide cleavage and deprotection include trifluoromethanesulfonic acid (TFMSA) and trimethylsilyltrifluoroacetate (TMSOTf).

The activity of molecules of the present invention can be measured using a variety of assays that measure for example, stimulation of gastrointestinal contractility, modulation of nutrient uptake, modulation of the secretion of digestive enzymes and hormones, modulation of secretion of enzymes and/or hormones in the pancreas, binding a TML/zsig33 receptor, or binding an antibody that specifically binds to residues 1 to 14 of SEQ ID NO:11. Of particular interest are changes in contractility of smooth muscle cells. For example, the contractile response of segments of mammalian duodenum or other gastrointestinal smooth muscles tissue (Depoortere et al., *J. Gastrointestinal Motility* 1:150–159, 1989, incorporated herein by reference). An exemplary in vivo assay uses an ultrasonic micrometer to measure the dimensional changes radially between commissures and longiturdinally to the plane of the valve base (Hansen et al., *Society of Thoracic Surgeons* 60:S384–390, 1995).

Gastric motility is generally measured in the clinical setting as the time required for gastric emptying and subsequent transit time through the gastrointestinal tract. Gastric emptying scans are well known to those skilled in the art, and briefly, comprise use of an oral contrast agent, such as barium, or a radiolabeled meal. Solids and liquids can be measured independently. A test food or liquid is radiolabeled with an isotope (e.g. $^{99m}$Tc), and after ingestion or administration, transit time through the gastrointestinal tract and gastric emptying are measured by visualization using gamma cameras (Meyer et al., *Am. J. Dig. Dis.* 21:296, 1976; Collins et al., *Gut* 24:1117, 1983; Maughan et al., *Diabet. Med.* 13 9 *Supp.* 5:S6–10, 1996 and Horowitz et al., *Arch. Intern. Med.* 145:1467–1472, 1985). These studies may be performed before and after the administration of a promotility agent to quantify the efficacy of the drug.

Assays measuring TML peptides ability to affect cell proliferation or differentiation are well known in the art. For example, assays measuring proliferation include such assays as chemosensitivity to neutral red dye (Cavanaugh et al., *Investigational New Drugs* 8:347–354, 1990, incorporated herein by reference), incorporation of radiolabelled nucleotides (Cook et al., *Analytical Biochem.* 179:1–7, 1989, incorporated herein by reference), incorporation of 5-bromo-2'-deoxyuridine (BrdU) in the DNA of proliferating cells (Porstmann et al., *J. Immunol. Methods* 82:169–179, 1985, incorporated herein by reference), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988; all incorporated herein by reference). Assays measuring differentiation include, for example, measuring cell-surface markers associated with stage-specific expression of a tissue, enzymatic activity, functional activity or morphological changes (Watt, *FASEB,* 5:281–284, 1991; Francis, *Differentiation* 57:63–75, 1994; Raes, *Adv. Anim. Cell Biol. Technol. Bioprocesses,* 161–171, 1989; all incorporated herein by reference).

Assays can be used to measure other cellular responses, that include, chemotaxis, adhesion, changes in ion channel influx, regulation of second messenger levels and neurotransmitter release. Such assays are well known in the art. See, for example, in "Basic & Clinical Endocrinology Ser., Vol. Vol. 3," *Cytochemical Bioassays: Techniques & Applications,* Chayen; Chayen, Bitensky, eds., Dekker, New York, 1983.

In view of the tissue distribution observed for zsig33, agonists (including the natural ligand/substrate/cofactor/synthetic and naturally occurring peptides, and variants, etc.) and antagonists have enormous potential in both in vitro and in vivo applications. Compounds identified as TML peptide agonists are useful for promoting stimulation of gastrointestinal contractility, modulation of nutrient uptake, modulation of the secretion of digestive enzymes and hormones, modulation of secretion of enzymes and/or hormones in the pancreas, binding a TML/zsig33 receptor, or binding an antibody that specifically binds to residues 1 to 14 of SEQ ID NO:11 in vivo and in vitro. For example, agonist compounds are useful as components of defined cell culture media and regulate the uptake of nutrients, and thus are useful in specifically promoting the growth and/or development of gastrointestinal cells such as G cells, enterochromaffin cells and the epithelial mucosa of the stomach, duodenum, proximal jejunum, antrum and fundus.

The family of gut-brain peptides has been associated with neurological and CNS functions. For example, NPY, a peptide with receptors in both the brain and the gut has been shown to stimulate appetite when administered to the central nervous system (Gehlert, *Life Sciences* 55(6):551–562, 1994). Motilin immunoreactivity has been identified in different regions of the brain, particularly the cerebellum, and in the pituitary (Gasparini et al., *Hum. Genetics* 94(6):671–674, 1994). Motilin has been found to coexist with neurotransmitter γ-aminobutyric acid in cerebellum (Chan-Patay, *Proc. Sym. 50th Anniv. Meet. Br. Pharmalog. Soc.:*1–24, 1982). Physiological studies have provided some evidence that motilin has an affect on feeding behavior (Rosenfield et al., *Phys. Behav.* 39(6):735–736, 1987), bladder control, pituitary growth hormone release. Other gut-brain peptides, such as CCK, enkephalin, VIP and secretin have been shown to be involved in control of blood pressure, heart rate, behavior, and pain modulation, in addition to be active in the digestive system. Therefore, TML peptides, could be expected to have some neurological association.

Additionally, other members of the gut-brain peptides, such as CCK, gastrin, and the like, have been shown to modulate secretion of pancreatic enzymes and hormones. Thus, TML peptides can be used to modulate secretion of pancreatic enzymes and hormones.

Similarly, other members of this family are known to modulate the secretion of endogenous proteins, such as the manner in which glucagon modulates the secretion of insulin. TML peptides can be used to modulate the secretion of non-TML proteins such as, for example, GLP-1, growth hormone, somatostatin, and the like.

Using site-specific changes in the amino acid and DNA sequences of the present invention analogs can be made that are either antagonists, agonists or partial agonists (Macielag et al., *Peptides: Chem. Struct. Biol.* pp.659, 1996). Antagonists are useful for clinical conditions associated with gastrointestinal hypermotility such as diarrhea and Crohn's disease. Antagonists are also useful as research reagents for characterizing sites of ligand-receptor interaction.

A TML peptide can also be used for purification of receptors. The peptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking peptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore™, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be used within other assay systems known in the art. Such systems include Scatchard analysis for determination of binding affinity (see Scatchard, *Ann. NY Acad. Sci.* 51: 660–72, 1949) and calorimetric assays (Cunningham et al., *Science* 253:545–48, 1991; Cunningham et al., *Science* 245:821–25, 1991).

TML peptides, and variants can also be used to prepare antibodies that specifically bind to TML epitopes or peptides. Methods for preparing polyclonal and monoclonal antibodies are well known in the art (see, for example, Sambrook et al., *Molecular Cloning: A Laboratory Manual, Second Edition*, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982, which are incorporated herein by reference). As would be evident to one of ordinary skill in the art, polyclonal antibodies can be generated from a variety of warm-blooded animals, such as horses, cows, goats, sheep, dogs, chickens, rabbits, mice, and rats.

The immunogenicity of a TML peptide may be increased through the use of an adjuvant, such as alum (aluminum hydroxide) or Freund's complete or incomplete adjuvant. Polypeptides useful for immunization also include fusion polypeptides, such as fusions of TML peptides or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as $F(ab')_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to TML protein or peptide, and selection of antibody display libraries in phage or similar vectors (for instance, through use of immobilized or labeled TML protein or peptide).

Antibodies are defined to be specifically binding if they bind to a TML peptide with a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art (for example, by Scatchard analysis).

A variety of assays known to those skilled in the art can be utilized to detect antibodies which specifically bind to TML proteins or peptides. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant TML protein or peptide.

Antibodies to TML peptides may be used for tagging cells that express TML peptides for isolating TML peptides by affinity purification; for diagnostic assays for determining circulating levels of TML peptides; for detecting or quantitating soluble TML peptides as marker of underlying pathology or disease; in analytical methods employing FACS; for screening expression libraries; for generating anti-idiotypic antibodies; and as neutralizing antibodies or as antagonists to block TML peptide activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications.

Molecules of the present invention can be used to identify and isolate receptors that mediate the function of TML peptides as well as zsig33 peptides. For example, proteins and peptides of the present invention can be immobilized on a column and membrane preparations run over the column (*Immobilized Affinity Ligand Techniques,* Hermanson et al., eds., Academic Press, San Diego, Calif., 1992, pp.195–202). Polypeptides and peptides which bind to the TML peptides and variants of the present invention can then be eluted and characterized using methods known in the art. Proteins and peptides can also be radiolabeled (*Methods in Enzymol.,* vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified in vivo and in vitro. Other detectable labels can also be used and include, for example, fluorescent labels (FITC, rhodamine, and fluorescent-biotinylated labels). Tissues which bind TML peptides can be identified, for example, by binding assays as shown in Example 10, herein. Such tissues can be used as sources of cell extracts, membrane fractions, protein lysates, purified protein, and the like, and applied to a column on which the TML peptides or variants have been immobilized and TML receptors can be isolated and characterized. Alternatively, such tissues can be harvested and tested in vitro or in vivo for binding to the TML ligand.

Another method to identify and purify the TML receptor measures the stimulation/inhibition of TML receptor-dependent cellular responses. For example, cell lines can be transfected with a reporter gene construct that is responsive to a receptor stimulated cellular pathway. Reporter gene constructs of this type are known in the art, and generally comprise a response element operably linked to a gene encoding an assay detectable protein, such as luciferase. DNA response elements can include, but are not limited to, cyclic AMP response elements (CRE), hormone response elements (HRE) insulin response element (IRE) (Nasrin et al., *Proc. Natl. Acad. Sci. USA* 87:5273–7, 1990) and serum response elements (SRE) (Shaw et al. *Cell* 56: 563–72, 1989). Cyclic AMP response elements are reviewed in Roestler et al., *J. Biol. Chem.* 263 (19):9063–6; 1988 and Habener, *Molec. Endocrinol.* 4 (8):1087–94; 1990. Hormone response elements are reviewed in Beato, *Cell* 56:335–44; 1989. The cell line can then be transfected with a cDNA library prepared from a tissue type which binds to TML peptides and variants, for example, kidney, duodenum, and jejunum, or others as identified by binding assays such as, for example, the assay in Example 10. Cell extracts, membrane fractions, protein lysates, purified protein, and the like, containing TML peptides and variants stimulate the transfected cell lines by binding to cells expressing the cDNA of the receptor. The binding of a TML peptide or variant thereof, to its receptor results in a change in the assayable protein or metabolite. Additionally, binding can be evidenced by the modulation of cyclic adenosine monophosphate (cAMP) or cyclic guanosine monophosphate (cGMP). Measuring changes in cAMP and cGMP is known to one skilled in the art, and kits are commercially available (Biotrak, Amersham Pharmacia Biotech, Piscataway, N.J.) for these determinations. In the alternative, cell extracts, membrane fractions, protein lysates, purified protein, and the like, containing TML peptides and variants can be tested for direct binding to cells transfected with both the cDNA library (which contains the receptor) and the reporter gene using TML peptides or variants tagged with a detectable label (e.g., $^{125}$I, biotin, horseradish peroxidase, FITC, and the like). Within assays of this type, the ability of a labeled test sample to bind to the receptor is indicative of ligand binding. Receptors used within binding assays may be cellular receptors or isolated, immobilized receptors.

As a ligand, the activity of TML peptide, or variant can be measured by a silicon-based biosensor microphysiometer which measures the extracellular acidification rate or proton excretion associated with receptor binding and subsequent physiologic cellular responses. An exemplary device is the Cytosensor™ Microphysiometer manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906–1912, 1992; Pitchford, S. et al., *Meth. Enzymol.* 228:84–108, 1997; Arimilli, S. et al., *J. Immunol. Meth.* 212:49–59, 1998; Van Liefde, I. et al., *Eur. J. Pharmacol.* 346:87–95, 1998. The microphysiometer can be used for assaying adherent or non-adherent eukaryotic or prokaryotic cells. By measuring extracellular acidification changes in cell media over time, the microphysiometer directly measures cellular responses to various stimuli, including TML peptide, variant, agonists, or antagonists. Preferably, the microphysiometer is used to measure responses of a TML peptide-responsive eukaryotic cell, compared to a control eukaryotic cell that does not respond to TML peptide, or variant. TML peptide-responsive eukaryotic cells comprise cells into which a receptor for TML peptide has been transfected creating a cell that is responsive to TML peptide, or variant; or cells naturally responsive to TML peptide such as, for example, cells derived from the kidney or small intestine. Differences, measured by a change in the response of cells exposed to TML peptide, or variant relative to a control not exposed to TML peptide, or variant, are a direct measurement of TML peptide-modulated cellular responses. Moreover, such TML peptide-modulated responses can be assayed under a variety of stimuli. The present invention provides a method of identifying agonists of TML peptides, comprising providing cells responsive to a TML peptides, culturing a first portion of the cells in the absence of a test compound, culturing a second portion of the cells in the presence of a test compound, and detecting a change in a cellular response of the second portion of the cells as compared to the first portion of the cells. The change in cellular response is shown as a measurable change in extracellular acidification rate. Moreover, culturing a third portion of the cells in the presence of TML peptide and the absence of a test compound can be used as a positive control for the TML peptide-responsive cells, and as a control to compare the agonist activity of a test compound with that of the TML peptide. Antagonists of TML peptides can be identified by exposing the cells to TML peptides in the presence and absence of the test compound, whereby a reduction in TML peptide-stimulated activity is indicative of antagonist activity in the test compound.

Moreover, TML peptides and variants can be used to identify cells, tissues, or cell lines which respond to a TML peptide-stimulated pathway. The microphysiometer, described above, can be used to rapidly identify ligand-responsive cells, such as cells responsive to TML peptides and variants of the present invention. Cells can be cultured in the presence or absence of TML peptides and variants. Those cells which elicit a measurable change in extracellular acidification in the presence of TML peptides and variants are responsive to zsig33. Such cell lines, can be used to identify antagonists and agonists of TML peptide as described above.

The chromosomal localization of zsig33 is 3p26.1 The present invention also provides reagents which will find use in diagnostic applications. For example, the TML gene, a probe comprising TML DNA or RNA or a subsequence thereof can be used to determine if the TML gene is present on chromosome 3p26.1 or if a mutation has occurred. Detectable chromosomal aberrations at the zsig33 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, Chest 108:255–65, 1995).

The peptides, variants, nucleic acid and/or antibodies of the present invention may be used in treatment of disorders associated with gastrointestinal contractility, secretion of digestive enzymes, hormones and acids, secretion of hormones in the pancreas and/or brain, gastrointestinal motility, recruitment of digestive enzymes; inflammation, particularly as it affects the gastrointestinal system; reflux disease and regulation of nutrient absorption. Specific conditions that will benefit from treatment with molecules of the present invention include, but are not limited to, diabetic gastroparesis, post-surgical gastroparesis, vagotomy, chronic idiopathic intestinal pseudo-obstruction and gastroesophageal reflux disease. Additional uses include, gastric emptying for radiological studies, stimulating gallbladder contraction and antrectomy.

The motor and neurological affects of molecules of the present invention make it useful for treatment of obesity and other metabolic disorders where neurological feedback modulates nutritional absorption. The molecules of the present invention are useful for regulating satiety, glucose absorption and metabolism, and neuropathy-associated gastrointestinal disorders.

Peptides of the present invention may be useful for evaluating functions of the hypothalamus-pituitary-adrenal axis by challenging the gastrointestinal system with TML peptides, including variants, and measuring gastric motility and contractility, modulation of nutrient uptake, modulation of the secretion of digestive enzymes and hormones, or modulation of secretion of enzymes and/or hormones in the pancreas.

Additionally, molecules of TML peptides may be used to detect or modulate the growth and/or differentiation of tumor cells which are expressing a receptor which binds to TML peptides. TML peptides can be labeled with radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. These labeled polypeptides can be applied in vitro or in vivo and are especially useful to identify TML or zsig33 receptors located on tumors in such tissues as, for example, stomach, brain, pancreas, kidney, duodenum, jejunum, and lung.

Molecules of the present invention are also useful as additives to anti-hypoglycemic preparations containing glucose and as adsorption enhancers for oral drugs which require fast nutrient action. Additionally, molecules of the present invention can be used to stimulate glucose-induced insulin release.

For pharmaceutical use, the proteins of the present invention are formulated for parenteral, nasal inhalation, particularly intravenous or subcutaneous, delivery according to conventional methods. Intravenous administration will be by bolus injection or infusion over a typical period of one to several hours. In general, pharmaceutical formulations will include a TML protein, peptides or variants in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 $\mu$g/kg of patient weight per day, preferably 0.5–20 $\mu$g/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. For example, a therapeutically effective amount of TML peptide is an amount sufficient to produce a clinically significant change in gastric motility and parameters used to measure changes in nutritional absorption. Specific tests for making such measurements are known to these ordinarily skilled in the art.

EXAMPLES

Example 1

Scanning of a cDNA database for cDNAs containing a secretion sequence revealed an expressed sequence tag (EST) that has homology to motilin. The cDNA is from a human fetal pancreatic cDNA library.

Confirmation of the EST sequence was made by sequence analyses of the cDNA from which the EST originated. This cDNA was contained in a plasmid, and was excised using cloning sites. The analyses revealed that the cDNA encompassed the entire coding region of the DNA encoding zsig33.

Example 2

Northerns were performed using Human Multiple Tissue Blots and Human RNA Master dot blots from Clontech (Palo Alto, Calif.). The probe was approximately 40 bp oligonucleotide ZC12,494 (SEQ ID NO: 7). The probe was end labeled using T4 Polynucleotide Kinase (Life Technologies, Inc., Gaithersburg, Md.) and T4 Polynucleotide Kinase Forward Buffer (Life Technologies, Inc.). The probe was purified using a NUCTRAP push columns (Stratagene, La Jolla, Calif.). EXPRESSHYB (Clontech) solution was used for prehybridization and as a hybridizing solution for the Northern blots. Hybridization took place at 42° C., and the blots were washed in 2×SSC and 0.05% SDS at RT, followed by a wash in 1×SSC and 0.1% SDS at 71° C. An approximately 600 bp transcript was observed as a strong signal in stomach, with weaker signals seen in pancreas and small intestine.

Example 3

Two male Sprague-Dawley rats, approximately 12 weeks old (Harlan, Indianapolis, Ind.) were anesthetized with urethane and their stomachs were exposed through a small abdominal incision. Two 2.4 mm transducing crystals (Sonometrics, Ontario, Canada) were placed on the antral portion of the stomach such that circular contractions could be monitored as a change in the distance between the two crystals. The crystals were attached with VETBOND TISSUE ADHESIVE (3M, St. Paul, Minn.).

10 $\mu$l of 1 $\mu$M acetylcholine was applied topically to the stomach between the two crystals, and resulted in a rapid, but transient increase in the distance between two crystals. 10 $\mu$l of norepinephrine (NE) at 1 $\mu$M caused a reduction in the distance between the two crystals. The amplitude of the NE-induced decrease was approximately 50% of the acetylcholine-induced increase in distance. Both responses were transient.

A negative control of 10 $\mu$l of phosphate buffer solution (PBS) applied topically between the crystals had no effect.

A 14 amino acid zsig33 peptide (from amino acid residue 24 (Gly) to amino acid residue 37 (Gln) of SEQ ID NO: 2) was dissolved in PBS) and 10 $\mu$l was applied topically for a final concentration of 1 $\mu$g, 10 $\mu$g or 100 $\mu$g. The zsig33 at 1 $\mu$g induced a sustained, rhythmic increase and decrease in crystal distance. This effect appeared to be dose-dependent, with enhanced responses in both rate and amplitude when of the contractions 10 $\mu$g and 100 $\mu$g were tested.

Example 4

Eight female ob/ob mice, approximately 6 weeks old (Jackson Labs, Bar Harbor, Me.) were adapted to a 4 hour daily feeding schedule for two weeks. After two weeks on the feeding schedule, the mice were give 100 $\mu$g of a 14 amino acid amino zsig33 peptide (from amino acid residue 24 (Gly) to amino acid residue 37 (Gln) of SEQ ID NO: 2) in 100 $\mu$l sterile 0.1% BSA by oral gavage, immediately after their eating period (post-prandially). Thirty minutes later, the mice were challenged orally with a 0.5 ml volume of 25% glucose. Retroorbital bleeds were done to determine serum glucose levels. Blood was drawn prior to zsig33 dosing, prior to oral glucose challenge, and at 1, 2, 4, and 20 hours following the glucose challenge.

When zsig33 peptide was given orally at 100 $\mu$g, 30 minutes prior to an oral glucose challenge, an enhanced post-prandial glucose absorption was seen.

Example 5 zsig33-1, a peptide corresponding to amino acid residue 24 (Gly) to amino acid residue 37 (Gln) of SEQ ID NO: 2, was synthesized by solid phase peptide synthesis using a model 431A Peptide Synthesizer (Applied Biosystems/ Perkin Elmer, Foster City, Calif.). Fmoc-Glutamine resin (0.63 mmol/g; Advanced Chemtech, Louisville, Ky.) was used as the initial support resin. 1 mmol amino acid cartridges (Anaspec, Inc. San Jose, Calif.) were used for synthesis. A mixture of 2(1-Hbenzotriazol-y-yl 1,1,3,3-tetrahmethylhyluronium hexafluorophosphate (HBTU), 1-hydroxybenzotriazol (HOBt), 2m N,N-Diisolpropylethylamine, N-Methylpyrrolidone, Dichloromethane (all from Applied Biosystems/Perkin Elmer) and piperidine (Aldrich Chemical Co., St. Louis, Mo.), and used for synthesis reagents.

The Peptide Companion software (Peptides International, Louisville, Ky.) was used to predict the aggregation potential and difficulty level for synthesis for the zsig33-1 peptide. Synthesis was performed using single coupling programs, according to the manufacturer's specifications.

The peptide was cleaved from the solid phase following standard TFA cleavage procedure (according to Peptide Cleavage manual, Applied Biosystems/Perkin Elmer). Purification of the peptide was done by RP-HPLC using a C18, 10 $\mu$m semi-peparative column (Vydac, Hesperial, Calif.). Eluted fractions from the column were collected and analyzed for correct mass and purity by electrospray mass spectrometry. Two pools of the eluted material were collected. The mass spectrometry analysis results indicated that both pools contained the purified form of zsig33 with a mass of 1600 Daltons. This was the expected mass, so the pools were combined, frozen and lyophilized.

Example 6 zsig33 was mapped to chromosome 3 using the commercially available "GeneBridge 4 Radiation Hybrid Panel" (Research Genetics, Inc., Huntsville, Ala.). The GeneBridge 4 Radiation Hybrid Panel contains DNAs from each of 93 radiation hybrid clones, plus two control DNAs (the HFL donor and the A23 recipient). A publicly available. WWW server allows mapping relative to the Whitehead Institute/ MIT Center for Genome Research's radiation hybrid map of the human genome (the "WICGR" radiation hybrid map) which was constructed with the GeneBridge 4 Radiation Hybrid Panel.

For mapping of zsig33 with the "GeneBridge 4 RH Panel", 20 $\mu$l reactions were set up in a 96-well microtiter plate (Stratagene, La Jolla, Calif.) and used in a "RoboCycler Gradient 96" thermal cycler (Stratagene). Each of the 95 PCR reactions consisted of 2 $\mu$l 10×KlenTaq PCR reaction buffer (CLONTECH Laboratories, Inc., Palo Alto, Calif.), 1.6 $\mu$l dNTPs mix (2.5 mM each, Perkin-Elmer, Foster City, Calif.), 1 $\mu$l sense primer, ZC13,166 (SEQ ID NO: 8), 1 $\mu$l antisense primer, ZC13,167 (SEQ ID NO: 9), 2 $\mu$l "Redi-Load" (Research Genetics, Inc., Huntsville, Ala.), 0.4 $\mu$l 50×Advantage KlenTaq Polymerase Mix (Clontech Laboratories, Inc.), 25 ng of DNA from an individual hybrid clone or control and ddH2O for a total volume of 20 $\mu$l. The reactions were overlaid with an equal amount of mineral oil and sealed. The PCR cycler conditions were as follows: an initial 1 cycle 5 minute denaturation at 95° C., 35 cycles of a 1 minute denaturation at 95° C., 1 minute annealing at 64° C. and 1.5 minute extension at 72° C., followed by a final 1 cycle extension of 7 minutes at 72° C. The reactions were separated by electrophoresis on a 3% NuSieve GTG agarose gel (FMC Bioproducts, Rockland, Me.).

The results showed that zsig33 maps 10.43 cR_3000 from the framework marker AFMA216ZG1 on the WICGR chromosome 3 radiation hybrid map. Proximal and distal framework markers were AFMA216ZG1 and D3S1263, respectively. The use of surrounding markers positions zsig33 in the 3p26.1 region on the integrated LDB chromosome 3 map (fbe Genetic Location Database, University of Southhampton, WWW server).

Example 7

The effect of topically applied zsig33 peptide (amino acid 24 to 37 of SEQ ID NO: 2) on the transit of phenol red through the stomachs of fasted male Sprague-Dawley rats (Harlan, Indianapolis, Ind.) was evaluated. The rats (6 animals, 8 weeks old) were fasted 24 hrs prior to being anesthetized with urethane(0.5 ml/100 grams of 25% solution). After anesthetizing, the animals were orally gavaged with 1 ml of Phenol Red solution (50 mg/ml in 2% methylcellulose solution).

The stomach of each animal was exposed through a small abdominal incision and either 1 μg zsig33 peptide or a 14 amino acid control of a scrambled sequence peptide was applied topically to the stomach five minutes following the gavage. The amount of Phenol Red remaining in the stomach was determined by measuring optical density of the extracted stomach contents 30 minutes after the gavage.

The zsig33 peptide reduced the amount of Phenol Red remaining in the stomach by approximately 25% compared to a scrambled peptide, indicating that the zsig33 peptide enhanced gastric emptying in these rats.

Example 8

Sixteen female ob/ob mice, 8 weeks old, (Jackson Labs, Bar Harbor, Me.) were adapted to a special 4 hour daily feeding schedule for two weeks. The were fed ad libitum from 7:30–11:30 am daily. After two weeks on the feeding schedule, the mice were divided into two groups of 8. One group was given 1.0 μg/mouse of zsig33-1 (14 amino acid peptide) and the other vehicle (a 14 amino acid scrambled sequence peptide) in 100 μl sterile 0.1% BSQA by oral gavage just prior to receiving food, and at the end of the 4 hour feeding period. The mice were injected twice daily for fourteen days, during which time food intake and body weight was measured daily. On day 14, immediately after the second oral gavage of the zsig33-1 peptide, the mice were challenged orally with an 0.5 ml volume of 25% glucose. Retro-orbital bleeds were done to determine serum glucose levels immediately prior to administration of the zsig33-1 peptide or vehicle (t=30 min.), and also at 0, 1, 2, and 4 hours following the glucose challenge.

Results indicated that when zsig33-1 given orally at 1 μg/mouse had no affect on daily body weight or food intake measurements, or on glucose clearance as determined on day 14.

Example 9

A. Gut Northern Tissue Blot

A Northern blot was prepared using mRNA from the following sources:
1. RNA from Human Colorectal Andenocarcinoma cell line SW480 (Clontech, Palo Alto, Calif.)
2. RNA from human small intestine tissue (Clontech)
3. RNA from human stomach tissue (Clontech)
4. Human Intestinal Smooth Muscle cell line (Hism; ATCC No.CRL-1692; American Type Culture Collection, 12301 Parklawn Drive, Rockville, Md.)
5. Normal Human Colon cell line (FHC; ATCC No. CRL-1831; American Type Culture Collection)
6. Human Normal Fetal Small Intestine cell line (FHs74 Int.; ATCC No. CCL241; American Type Culture Collection).

Total RNAs were isolated from Hism, FHC and FHs74 Int. by acid guanidium method (Chomczynski et al., *Anal. Biochem.* 162:156–159, 1987). The polyA$^+$ RNAs were selected by eluting total RNA through a column that retains polyA+RNAs (Aviv et al., *Proc. Nat. Acad. Sci.* 69:1408–1412, 1972). 2 μg of polyA$^+$ RNA from each sample was separated out in a 1.5% agarose gel in 2.2 M formaldehyde and phosphate buffer. The RNAs were transferred onto Nytran membrane (Schleicher and Schuell, Keene, N.H.) in 20×SSC overnight. The blot was treated in the UV Stratalinker 2400 (Stratagene, La Jolla, Calif.) at 0.12 Joules. The bolt was then baked at 80° C. for one hour.

Using the full length cDNA (shown in SEQ ID NO: 1) amplified by PCR approximately 50 ng of zsig33 DNA and 42.5 μl of water was radiolabeled with $^{32}$P dCTP using a Rediprime pellet kit (Amersham, Arlington Heights, Ill.) according to the manufacturer's specifications. The blot was hybridized in EXPRESSHYB (Clontech) at 55° C. overnight. The blot was washed at room temp. in 2×SSC and 0.1% SDS, then in 2×SSC and 0.1% SDS at 65° C., and finally at 65° C. in 0.1×SSC and 0.1% SDS. Results showed that zsig33 hybridized to stomach RNA and not to other RNAs from other tissue origins.

B. Tumor Northern Blot

A Northern Territory™—Human Tumor Panel Blot II (Invitrogen, San Diego, Calif.) and a Northern Territory™—Human Stomach Tumor Panel Blot (Invitrogen) were analyzed for expression patterns of zsig33 RNA.

The Human Tumor Panel Blot contained 20 μg of total RNA per lane and was run on a 1% denaturing formaldehyde gel. The blot contained RNA from: esophageal tumor, normal esophagus, stomach tumor, normal stomach, colon tumor, normal colon, rectal tumor and normal rectum. The Stomach Tumor Panel Blot contained total RNA isolated human and normal tissues of four separate donors. 20 μg of RNA was used for each sample lane and the lanes alternated a normal and tumor set from each donor.

Probes that were approximately 40 bp oligonucleotide ZC12,494 (SEQ ID NO: 7) were prepared. The probes were end labeled using T4 Polynucleotide Kinase (Life Technologies, Inc., Gaithersburg, Md.) and T4 Polynucleotide Kinase Forward Buffer (Life Technologies, Inc.). The probes were purified using a NUCTRAP push columns (Stratagene, La Jolla, Calif.). The tumor blot and the stomach blot were both treated in the same way. EXPRESSHYB (Clontech) solution was used for prehybridization and as a hybridizing solution for the Northern blots. Hybridization took place at 42° C., and the blots were washed in 0.1×SSC and 0.01% SDS at 60° C., followed by a wash in 0.1×SSC and 0.1% SDS at 70° C. The results clearly indicate that zsig33 is exclusively expressed in normal stomach tissue in both the Human Tumor Panel and the Human Stomach Tumor Panel.

Example 10

Ten week old Balb C male mice were anesthetized via intramuscular injection and tested for binding of TML peptides in vivo.

Two peptides were tested: the first peptide consisted of residues 1 to 14 of SEQ ID NO:11, and the second peptide consisted of residues 1 to 18 of SEQ ID NO.11. A single glycine was used as a negative control. Additionally, a "scrambled" negative control consisting of residues the first peptide which had been rearranged (SEQ ID NO:13) was also tested. The peptides and controls were coupled to fluorescein isothiocyantate (FITC, Molecular Probes, Eugene, Oreg.) in the following manner: The peptides, glycine control and FITC were dissolved in 0.1 M sodium bicarbonate at pH 9.0 to a concentration of 2.0 mg/ml for the peptides and glycine control and 5 mg/ml for FITC, avoiding exposure of the FITC to strong light. The FITC/sodium bicarbonate solution was added to the peptides at a ratio of 1 mg FITC to 1 mg peptide or glycine control, and allowed to react in the dark at ambient room temperature for 1 hour. The FITC-conjugated peptides and glycine control were dialyzed in a 1 K dialysis membrane and 0.1 M sodium bicarbonate buffer at 4° C. The buffer was changed daily and unbound FITC in the post-dialyzed buffer was measured by HPLC. After six days, the buffer was changed to phosphate buffered saline (PBS) and dialyzed for two days followed by another change in PBS and dialyzed for another 2 days. Peptide- or glycine-bound FITC was determined by measuring the absorbance of the dialyzed FITC-bound material at 498 nm and dividing by the extinction coefficient of fluorescein, 0.083 $\mu$M. The molar ratio of fluorescein to peptide (mole FITC/mole peptide) was then determined.

The labeled peptides were administered via tail vein injections such that each mouse received 0.5 ml (0.5 mg) of labeled peptide which was allowed to circulate in the mice for 15 minutes following injection.

While under anesthesia the right atrium of each mouse was snipped to allow an exit path and 20 ml of PBS was injected into left ventricle and used to flush the circulatory system. The mice were then perfused with approximately 10 ml of formalin in neutral buffer (10% Neutral Buffered Formalin (NBF), Surgipath, Richmond, Ill.).

Tissues of liver, kidney, heart, lung, thymus, spleen, duodenum, ileum, jejunum colon and stomach were harvested by dissection, and fixed overnight in 10% NBF before processing for histological evaluation. Tissues were processed in the V.I.P. 2000 (Miles, Inc., Elkhart, Ind.) resulting in Paraffin® infiltration of the tissue. The tissue/Paraffin® blocks were sliced into 5$\mu$m sections in a Jung Biocut (Leica, Nussloch, Germany), placed on glass slides, and incubated at 60° C. for one hour to aid in adhering the tissue to the slide. The Paraffin® was removed by washing the slides three times in 100% xylene for 5 minutes. The slides were then rehydrated by 2 washes in 100% ethanol for 3 minutes; followed by one wash in 95% ethanol. The slides were allowed to dry and then mounted with 5 to 10 $\mu$l of antifade medium [nine parts glycerol containing 2% DABCO (1,4-diazobicyclo-(2,2,2,)-octane, Sigma, St. Louis, Mo.), dissolved at 55–70° C.; one part 0.2 M Tris/HCL, pH 7.5 DAPI (Sigma, St. Louis, Mo.) or propididum iodide (0.5 $\mu$g/ml]. See also Kievits, T. et al., *Cytogenet Cell Cenet* 53:134–136 (1990) for antifade medium. Slides were covered with cover slips and immediately examined by fluorescent microscopy at 495 nm.

Results indicate the labeled peptides showed increased fluorescence in duodenum, jejunum and in the collecting ducts and convoluted tubules of the kidney compared to the glycine and "scrambled" controls. Other tissues showed similar fluorescence compared to the negative controls.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. An isolated polypeptide molecule selected from the group consisting of:
   a) a polypeptide molecule consisting of residues 1 to 10 as shown in SEQ ID NO:11;
   b) a polypeptide molecule consisting of residues 1 to 11 as shown in SEQ ID NO:11;
   c) a polypeptide molecule consisting of residues 2 to 11 as shown in SEQ ID NO:11;
   d) a polypeptide molecule consisting of residues 2 to 14 as shown in SEQ ID NO:11;
   e) a polypeptide molecule consisting of residues 3 to 14 as shown in SEQ ID NO:11;
   f) a polypeptide molecule consisting of residues 2 to 18 as shown in SEQ ID NO:11; and
   g) a polypeptide molecule consisting of residues 3 to 18 as shown in SEQ ID NO:11.

2. A polypeptide molecule consisting of residues 1 to 10 as shown in SEQ ID NO:11.

3. A polypeptide molecule consisting of residues 1 to 11 as shown in SEQ ID NO:11.

4. A polypeptide molecule consisting of residues 2 to 11 as shown in SEQ ID NO:11.

5. A polypeptide molecule consisting of residues 2 to 14 as shown in SEQ ID NO:11.

6. A polypeptide molecule consisting of residues 3 to 14 as shown in SEQ ID NO:11.

7. A polypeptide molecule consisting of residues 2 to 18 as shown in SEQ ID NO:11.

8. A polypeptide molecule consisting of residues 3 to 18 as shown in SEQ ID NO:11.

9. An isolated polypeptide molecule selected from the group consisting of:
   a) a polypeptide molecule consisting of residues 4 to 14 as shown in SEQ ID NO:11; and
   b) a polypeptide molecule consisting of residues 4 to 18 as shown in SEQ ID NO:11.

10. A polypeptide molecule consisting of residues 4 to 14 as shown in SEQ ID NO:11.

11. A polypeptide molecule consisting of residues 4 to 18 as shown in SEQ ID NO:11.

* * * * *